United States Patent [19]  [11] 3,934,034
Manning  [45] Jan. 20, 1976

[54] HYDROXY SUBSTITUTED DIPHENYLALKYLS FOR TREATMENT OF LIPIDEMIA

[75] Inventor: Robert E. Manning, Mountain Lakes, N.J.

[73] Assignee: Sandoz, Inc., E. Hanover, N.J.

[22] Filed: Aug. 9, 1973

[21] Appl. No.: 386,947

Related U.S. Application Data

[63] Continuation-in-part of Ser. No. 282,316, Aug. 21, 1972, abandoned, which is a continuation-in-part of Ser. No. 153,416, June 15, 1971, abandoned, which is a continuation-in-part of Ser. No. 100,533, Dec. 21, 1970, abandoned, which is a continuation-in-part of Ser. No. 60,745, Aug. 3, 1970, abandoned.

[52] U.S. Cl. ............... 424/346; 424/80; 424/361; 424/362; 424/363
[51] Int. Cl.$^2$ ......................................... A61K 31/05
[58] Field of Search ............... 260/619 A; 424/346

[56] References Cited
UNITED STATES PATENTS

| | | | |
|---|---|---|---|
| 2,617,832 | 11/1952 | Martin | 260/619 A |
| 2,651,572 | 9/1953 | Bickoff | 260/619 A X |
| 2,925,444 | 2/1960 | Levine et al. | 260/619 A |
| 3,529,066 | 9/1970 | Barnhart | 424/346 |
| 3,671,644 | 6/1972 | Irani et al. | 424/346 |

FOREIGN PATENTS OR APPLICATIONS

| | | | |
|---|---|---|---|
| 38,66M | 1/1966 | France | 424/346 |

*Primary Examiner*—Sam Rosen
*Assistant Examiner*—Vera C. Clarke
*Attorney, Agent, or Firm*—Gerald D. Sharkin; Robert S. Honor; Thomas O. McGovern

[57] ABSTRACT

Certain hydroxy diphenylalkyls, e.g., nordihydroguairetic acid, are useful as hypolipidemic agents.

19 Claims, No Drawings

HYDROXY SUBSTITUTED DIPHENYLALKYLS FOR TREATMENT OF LIPIDEMIA

This application is a continuation in part of U.S. Pat. Application Ser. No. 282,316 filed Aug. 21, 1972, now abandoned, which in turn is a continuation in part of U.S. Pat. Application Ser. No. 153,416 filed June 15, 1971, now abandoned, which in turn is a continuation in part of U.S. Pat. Application Ser. No. 100,533 filed Dec. 21, 1970, now abandoned, which in turn is a continuation in part of U.S. Pat. Application Ser. No. 60,745 filed Aug. 3, 1970, now abandoned.

This invention relates to the pharmaceutical activity of diphenyl alkyl derivatives. More particularly, this invention concerns the use of hydroxy substituted diphenylalkyls in the treatment of lipidemia in mammals. The invention also relates to pharmaceutical compositions containing the above compounds as an active ingredient thereof.

The active agents with which this invention is concerned may be represented by the following structural formula:

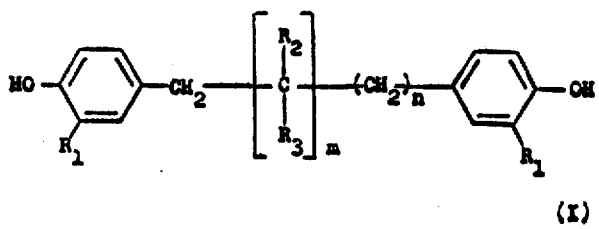

(I)

where
  m is 0, 1 or 2;
  n is 0 or 1;
  $R_1$ represents hydrogen or hydroxy; and
  $R_2$ and $R_3$ each independently represent hydrogen or methyl provided that when m is 0, n is 0 and that when m is 1 or 2 n is 1 and $R_1$ is hydroxy and that when m is 2, each
  $R_2$ can be the same or different and each $R_3$ can be the same or different and pharmaceutically acceptable salts thereof.

Preferred compounds of formula I are bis(p-hydroxyphenyl)methane and 1,4-bis (3,4-dihydroxyphenyl)-2,3-dimethylbutane (nordihydroguairetic acid).

The compounds of formula I above are known and may be prepared according to methods disclosed in the literature from known materials. The pharmaceutically acceptable salts may be mono- or di-salts and include the alkali metal salts, in particular, the sodium and potassium salts and the alkaline earth metal salts, such as the magnesium and calcium salts. These salts may also be prepared by methods disclosed in the literature. The present invention contemplates only the novel use of such compounds in pharmaceutical applications, particularly as hypolipidemic agents.

As previously indicated, the compounds of formula (I) are useful because they possess pharmacological activity in animals, e.g., mammals. In particular, the compounds of formula (I) are useful as hypolipidemic agents in the treatment of lipidemia, in particular, hyperlipoproteinemia as indicated by the fall in cholesterol and/or triglyceride levels in male albino Wistar rats weighing 110–130 g. initially. The rats are maintained on drug-free laboratory chow diet for seven days and then divided into groups of 8 to 10 animals. Each group with the exception of the control is then given the compound orally at a dose of 7.5, 30, 250 or 500 milligrams per kilogram of body weight per day, p.o. for six days. At the end of this period, the animals are anesthetized with sodium hexobarbital and bled from the carotid arteries. Serum or plasma samples are then extracted with isopropanol, and the cholesterol content of the extracts is estimated on a Technicon Autoanalyzer by standard methodology. For example, 1.0 ml. of serum is added to 9.0 ml. redistilled isopropanol. Two autoanalyzer cupsful of a mixture of zeolite-copper hydroxide and Lloydds reagent (Kersler, E., and Lederer, H., 1965, Technicon Symposium, Madiad Inc., New York, 345–347) are added, and the mixture is shaken for 1 hour. Cholesterol levels are determined using this sample by the standard Technicon N 24A (cholesterol) methodology. The mean total serum cholesterol levels are then computed and the hypocholesterolemic activity is expressed as the fall in cholesterol levels as a percentage of the control level. For the triglyceride determination, blood samples are collected as above and 1.0 ml samples of the serum are added to 9.0 ml redistilled isopropanol. Two autoanalyzer cupsful of a mixture of zeolite-copper hydroxide and Lloydds reagent (Kessler, G., and Lederer, H., 1965, Technicon Symposium, Mediad Inc., New York, 345–347) are added, and the mixture is shaken for one hour. After centrifugation, 2 ml of the clear supernates are evaporated to dryness and saponified by addition of 0.1 ml 10% KOH in 90% ethanol and 1.0 ml Skelly B (petroleum ether bp 60°-70°). After acidification and the removal of fatty acids with petroleum ether, the aqueous phases are neutralized, suitably diluted with water, and analyzed for glycerol by the method of Lofland (Anal. Biochem. 9, 393, 1964) using the Technicon Autoanalyzer. The change in serum triglyceride levels induced by the drug is computed as a percentage of the control triglyceride levels.

For such usage, the compounds are administered orally as such or admixed with conventional pharmaceutical carriers. They may be administered in such forms as tablets, dispersible powders, granules, capsules, syrups and elixirs. The compositions may contain one or more conventional adjuvants, such as sweetening agents, flavoring agents, coloring agents and preserving agents, in order to provide an elegant and palatable preparation. Tablets may contain the active ingredient in admixture with conventional pharmaceutically acceptable excipients, e.g., inert diluents, such as calcium carbonate, sodium carbonate, lactose and talc, granulating and disintegrating agents, e.g., starch and alginic acid, binding agents, e.g., starch, gelatin and acacia, and lubricating agents, e.g., magnesium stearate, stearic acid and talc. The tablets may be uncoated or coated by known techniques to delay disintegration and absorption in the gastro-intestinal tract and thereby provide a sustained action over a longer period. Similarly, oral liquids, e.g. suspensions may contain the active ingredient in admixture with any of the conventional excipients utilized for the preparation of such compositions, e.g., suspending agents (methylcellulose, tragacanth and sodium alginate), wetting agents (lecithin, polyoxyethylene stearate and polyoxyethylene sorbitan mono-oleate) and preservatives (ethyl-o-hydroxybenzoate). Capsules may contain the active ingredient alone or admixed with an inert solid diluent, e.g., calcium carbonate, calcium phosphate and kaolin. These pharmaceutical preparations may contain up to about 90% of the active ingredient in combination with the carrier or adjuvant.

The anti-hyperlipidemic effective dosage of the compounds of formula I employed for the alleviation of lipidemia may vary depending on the particular compound employed and the severity of the condition being treated. However, in general, satisfactory results are obtained when the compounds of formula (I) are administered at a daily dosage of from about 2 milligrams to about 500 milligrams per kilogram of animal body weight, p.o. preferably given in divided doses two to four times a day, or in sustained release form. The preferred dosage for the salt forms is 10 milligrams to 500 milligrams per kilogram of animal body weight p.o. For most large mammals, the total daily dosage is from about 150 to about 4000 milligrams. In the acid form, the preferred daily dosage is 150 to 2000 milligrams; and in the salt form, the preferred daily dose is 600 to 4000 milligrams. Dosage forms suitable for internal use comprise from about 37.5 to about 1000 milligrams of the active compound in acid form or 150 to 2000 milligrams in salt form in intimate admixture with a solid or liquid pharmaceutically acceptable carrier or diluent.

The preferred pharmaceutical compositions from the standpoint of preparation and ease of administration are solid compositions, particularly hard-filled capsules and tablets containing from about 50 to 250 milligrams of the active ingredient in acid form and 300 milligrams in salt form.

EXAMPLE 1

Tablets — Tablets suitable for oral administration which contain the following ingredients may be prepared by conventional tabletting techniques. Such tablets are useful in treating lipidemia at a dose of one or two tablets 2 to 4 times a day.

| Ingredients | Weight (mg.) |
|---|---|
| Nordihydroguairetic Acid | 50 |
| Tragacanth | 10 |
| Lactose | 197.5 |
| Corn Starch | 25 |
| Talcum | 15 |
| Magnesium Stearate | 2.5 |

EXAMPLE 2

Dry Filled Capsules — Capsules suitable for oral administration which contain the following ingredients are prepared in a conventional manner. Such capsules are useful in treating lipidemia at a dose of one capsule 2 to 4 times a day.

| Ingredients | Weight (mg.) |
|---|---|
| Nordihydroguairetic Acid | 100 |
| Inert solid diluent (starch, lactose, kaolin) | 200 |

EXAMPLES 3 and 4

Sterile Suspension for Injection and Oral Liquid Suspension

The following pharmaceutical compositions are formulated with the indicated amount of active agent using conventional techniques. The injectable suspension and the oral liquid suspension represent formulations useful as unit doses and may be administered in the treatment of lipidemia. The injectable suspension is suitable for administration once or twice a day whereas the oral liquid suspension is suitable administered 2 to 4 times per day for this purpose:

| Ingredients | Weight (mg.) sterile injectable suspension | oral liquid suspension |
|---|---|---|
| Nordihydroguairetic acid | 150 | 100 |
| Sodium carboxy methylcellulose U.S.P. | 1.25 | 12.5 |
| methylcellulose | 0.4 | — |
| Polyvinylpyrrolidone | 5 | — |
| Lecithin | 3 | — |
| Benzyl alcohol | 0.01 | — |
| Magnesium aluminum silicate | — | 47.5 |
| Flavor | — | q.s. |
| Color | — | q.s. |
| Methyl paraben U.S.P. | — | 4.5 |
| Propyl paraben U.S.P. | — | 1.0 |
| Polysorbate 80 (e.g. Tween 80) U.S.P. | — | 5 |
| Sorbitol solution 70% U.S.P. | — | 2,500 |
| Buffer agent to adjust pH for desired stability | q.s. | q.s. |
| Water | for injection q.s. to 1 ml. | q.s. to 5 ml. |

EXAMPLES 5 and 6

Tablets and Capsules Suitable For Oral Administration

Tablets and capsules containing the ingredients indicated below may be prepared by conventional techniques and are useful in treating lipidemia at a dose of one or two tablets or capsules 2 to 4 times a day.

| Ingredient | Weight (mg) tablet | capsule |
|---|---|---|
| bis (p-hydroxyphenyl) methane | 50 | 50 |
| tragacanth | 10 | — |
| lactose | 197.5 | 250 |
| corn starch | 25 | |
| talcum | 15 | |
| magnesium stearate | 2.5 | |
| | 300 mg. | 300 mg. |

Similarly, tablets and capsules can be prepared using the disodium salt of bis-(p-hydroxyphenyl)methane in place of the bis (p-hydroxyphenyl)methane at the same dosage level and used in treating lipidemia.

EXAMPLES 7 and 8

Sterile Suspension for Injection and Oral Liquid Suspension

The following pharmaceutical compositions are formulated with the indicated amount of active agent using conventional techniques. The injectable suspension and the oral liquid suspension represent formulations useful as unit doses and may be administered in the treatment of hyperlipidemia. The injectable suspension is suitable for administration once or twice a day whereas the oral liquid suspension is suitably administered 2 to 4 times per day for this purpose.

| Ingredients | Weight (mg). sterile injectable suspension | oral liquid suspension |
| --- | --- | --- |
| bis (p-hydroxyphenyl) methane | 150 | 100 |
| sodium carboxy methyl cellulose USP | 1.25 | 12.5 |
| methyl cellulose | 0.4 | — |
| polyvinylpyrrolidone | 5 | — |
| lecithin | 3 | — |
| benzyl alcohol | 0.01 | — |
| magnesium aluminum silicate | — | 47.5 |
| flavor | — | q.s. |
| color | — | q.s. |
| methyl paraben, U.S.P. | — | 4.5 |
| propyl paraben, U.S.P. | — | 1.0 |
| polysorbate 80 (e.g. Tween 80), U.S.P. | — | 5 |
| sorbitol solution, 70% U.S.P. | — | 2,500 |
| buffer agent to adjust pH for desired stability | q.s. | q.s. |
| water | for injection q.s. to 1 ml. | q.s. to 5 ml. |

Similarly, injectable solutions and suspension and oral liquid solutions and suspensions may be prepared by conventional techniques using the disodium salt of bis-(p-hydroxyphenyl)methane at the above dosage levels and used in the treatment of lipidemia.

EXAMPLES 9 AND 10

Tablets and Capsules Suitable For Oral Administration

Tablets and capsules containing the ingredients indicated below may be prepared by conventional techniques and are useful in treating lipidemia at a dose of one or two tablets or capsules 2 to 4 times a day.

| Ingredient | Weight (mg) tablet | capsule |
| --- | --- | --- |
| Disodium salt form of bis(p-hydroxyphenyl)methane | 300 | 300 |
| tragacanth | 10 | — |
| lactose | 297.5 | 300 |
| corn starch | 25 | — |
| talcum | 15 | — |
| magnesium stearate | 2.5 | — |
| | 650 mg. | 600 mg. |

EXAMPLES 11 AND 12

Sterile Suspension for Injection and Oral Liquid Suspension

The following pharmaceutical compositions are formulated with the indicated amount of active agent using conventional techniques. The injectable suspension and the oral liquid suspension represent formulations useful as unit doses and may be administered in the treatment of hyperlipidemia. The injectable suspension is suitable for administration twice a day whereas the oral liquid suspension is suitable administered 2 to 4 times per day for this purpose.

| Ingredients | Weight (mg). sterile injectable suspension | oral liquid suspension |
| --- | --- | --- |
| Disodium salt of bis (p-hydroxyphenyl) methane | 300 | 300 |
| sodium carboxy methyl cellulose USP | 1.25 | 12.5 |
| methyl cellulose | 0.4 | — |
| polyvinylpyrrolidone | 5 | — |
| lecithin | 3 | — |
| benzyl alcohol | 0.01 | — |
| magnesium aluminum silicate | — | 47.5 |
| flavor | — | q.s. |
| color | — | q.s. |
| methyl paraben, U.S.P. | — | 4.5 |
| propyl paraben, U.S.P. | — | 1.0 |
| polysorbate 80 (e.g. Tween 80), U.S.P. | — | 5 |
| sorbitol solution, 70% U.S.P. | — | 2,500 |
| buffer agent to adjust pH for desired stability | q.s. | q.s. |
| water | for injection q.s. to 1 ml. | q.s. to 5 ml. |

Compositions useful in treating lipidemia analogous to those of Examples 9 to 12 may be formulated by employing, in place of the sodium salt form of bis-(p-hydroxyphenyl)methane, the dipotassium, calcium or magnesium salt form thereof.

What is claimed is:

1. A method for treating lipidemia, which comprises orally administering to a mammal in need of said treatment an anti-hyperlipidemic effective amount of a compound of the formula:

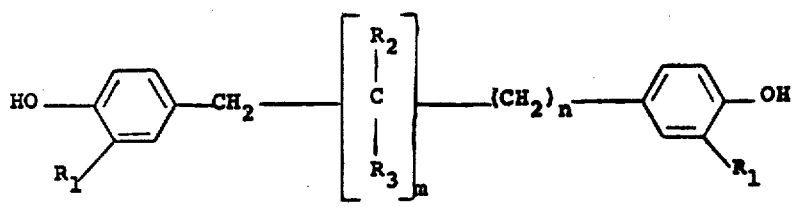

where
m is 0, 1 or 2;
n is 0 or 1;
$R_1$ represents hydrogen or hydroxy; and
$R_2$ and $R_3$ each independently represents hydrogen or methyl provided that when m is 0, n is 0 and that when m is 1 or 2, n is 1 and $R_1$ is hydroxy and that when m is 2 each $R_2$ can be the same or different and each $R_3$ can be the same or different or a pharmaceutically acceptable alkali or alkaline earth metal salt thereof.

2. The method according to claim 1 wherein the compound is administered at a daily dose of from about 150 milligrams to about 2000 milligrams.

3. The method according to claim 1 wherein the compound is administered in a unit dosage form comprising said compound to the extent of from about 37.5 milligrams to about 1000 milligrams per unit dosage.

4. The method according to claim 1 in which the compound is nordihydroguairetic acid.

5. The method according to claim 1 in which the compound is bis(p-hydroxyphenyl)methane.

6. A method for treating lipidemia, which comprises orally administering to a mammal in need of said treatment an antihyperlipidemic effective amount of a compound of the formula

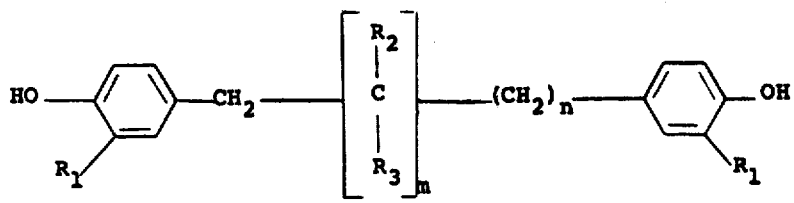

in pharmaceutically acceptable alkali or alkaline earth metal salt form,
where m, n, $R_1$, $R_2$, $R_3$ and the proviso are as set out in claim 10.

7. The method according to claim 6 wherein the compound is administered at a daily dose of from about 600 milligrams to about 4000 milligrams.

8. The method according to claim 6 wherein the compound is administered in a unit dosage form comprising said compound to the extent of from about 300 milligrams to about 2000 milligrams per unit dosage.

9. The method according to claim 6 in which the compound is disodium bis (p-hydroxyphenyl)methane.

10. A pharmaceutical composition in solid form useful in the treatment of lipidemia in mammals comprising bis(p-hydroxyphenyl) methane as the active ingredient thereof, and a pharmaceutically acceptable carrier therefore, said active ingredient being present in said composition from about 150 milligrams to about 4000 milligrams.

11. The pharmaceutical composition of claim 10, wherein said active ingredient is present in said composition from about 150 milligrams to about 2000 milligrams.

12. The pharmaceutical composition of claim 11, wherein said active ingredient is present in said composition from about 37.5 milligrams to about 1000 milligrams.

13. The composition according to claim 11, wherein said carrier is a solid orally ingestible carrier and the active ingredient is present in said composition from about 50 to 250 milligrams.

14. The pharmaceutical composition according to claim 10, wherein said active ingredient is in the form of a pharmaceutically acceptable alkali or alkaline earth metal salt and is present from about 600 milligrams to about 4000 milligrams.

15. The pharmaceutical composition of claim 14, wherein said active ingredient is present in said composition from about 150 milligrams to about 2000 milligrams.

16. The composition according to claim 10, wherein said carrier is a solid orally ingestible carrier and the active ingredient is in the form of a pharmaceutically acceptable alkali or alkaline earth metal salt and is present in said composition from about 300 milligrams.

17. A composition according to claim 10, in the form of a tablet.

18. The composition according to claim 14 in which the active ingredient is disodium bis (p-hydroxyphenyl)methane.

19. A tablet useful in the treatment of lipidemia in mammals comprising bis(p-hydroxyphenyl) methane as the active ingredient thereof and a pharmaceutically acceptable carrier therefor, said active ingredient being present in said tablet from about 50 to 250 milligrams.

* * * * *